(12) United States Patent
Haines et al.

(10) Patent No.: US 6,197,064 B1
(45) Date of Patent: *Mar. 6, 2001

(54) PROSTHETIC IMPLANT

(75) Inventors: Timothy G. Haines, Minneapolis, MN (US); David B. Goldstein, Weehawken, NJ (US)

(73) Assignee: Hudson Surgical Design, Inc., Weehawken, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/261,528

(22) Filed: Mar. 3, 1999

Related U.S. Application Data

(60) Continuation of application No. 08/892,286, filed on Jul. 14, 1997, now Pat. No. 5,879,354, which is a division of application No. 08/649,465, filed on May 17, 1996, now Pat. No. 5,755,803, which is a continuation-in-part of application No. 08/603,582, filed on Feb. 20, 1996, now Pat. No. 5,810,827, which is a continuation-in-part of application No. 08/300,379, filed on Sep. 2, 1994, now Pat. No. 5,514,139, said application No. 08/603,582, filed on Feb. 20, 1996, now Pat. No. 5,810,827, is a continuation-in-part of application No. 08/479,363, filed on Jun. 7, 1995, now Pat. No. 5,643,272, which is a continuation-in-part of application No. 08/342,143, filed on Nov. 18, 1994, now Pat. No. 5,597,379, which is a continuation-in-part of application No. 08/300,379, said application No. 08/479,363, is a continuation-in-part of application No. 08/300,379, said application No. 08/603,582, is a continuation-in-part of application No. 08/342,143, which is a continuation-in-part of application No. 08/300,379.

(51) Int. Cl.[7] .................................................. A61F 2/38

(52) U.S. Cl. ................................................ 623/20.31

(58) Field of Search ..................... 623/20.14, 20.15, 623/20.3, 20.31

(56) References Cited

U.S. PATENT DOCUMENTS

| 3,798,679 | * | 3/1974 | Ewald | 3/1 |
| 3,816,855 | * | 6/1974 | Saleh | 3/1 |
| 4,178,641 | * | 12/1979 | Tal | 623/20 |
| 4,353,135 | | 10/1982 | Forte et al. | 3/1.911 |
| 4,358,859 | | 11/1982 | Schurman et al. | 3/1.911 |
| 4,457,307 | | 7/1984 | Stillwell | 128/317 |
| 4,474,177 | | 10/1984 | Whiteside | 128/303 |
| 4,487,203 | | 12/1984 | Androphy | 128/303 |
| 4,566,448 | | 1/1986 | Rohr, Jr. | 128/92 |
| 4,568,348 | | 2/1986 | Johnson et al. | 623/20 |
| 4,586,933 | | 5/1986 | Shoji et al. | 623/20 |
| 4,653,488 | | 3/1987 | Kenna | 128/92 |
| 4,662,889 | | 5/1987 | Zichner et al. | 623/20 |
| 4,721,104 | | 1/1988 | Kaufman et al. | 128/92 |
| 4,722,330 | | 2/1988 | Russell et al. | 128/92 |
| 4,736,737 | | 4/1988 | Fargie et al. | 128/92 |
| 4,770,663 | | 9/1988 | Hanslik et al. | 623/20 |
| 4,787,383 | | 11/1988 | Kenna | 128/303 |
| 4,822,365 | | 4/1989 | Walker et al. | 623/20 |

(List continued on next page.)

FOREIGN PATENT DOCUMENTS

| 0538153 | 9/1992 | (EP) . |
| 577020 | 10/1977 | (RU) . |

*Primary Examiner*—David J. Isabella
(74) *Attorney, Agent, or Firm*—Wolff & Samson

(57) ABSTRACT

An implant is provided for which has an outer bearing surface and an inner attachment surface. The outer bearing surface functions as a joint contact surface for a reconstructed bone joint. The inner attachment surface contacts a bone and is attached thereto. The inner attachment surface of the implant is curvilinear from the anterior to the posterior area of the femur, and is also curvilinear from the medial to the lateral areas of the femur to approximates the shape of natural femur. The resection of the femur for accommodating the implant can be properly performed by a milling device employing one or more curvilinear milling bits.

16 Claims, 7 Drawing Sheets

U.S. PATENT DOCUMENTS

| | | | |
|---|---|---|---|
| 5,002,545 | 3/1991 | Whiteside et al. | 606/80 |
| 5,053,037 | 10/1991 | Lackey | 606/79 |
| 5,098,436 | 3/1992 | Ferrante et al. | 606/88 |
| 5,100,409 | 3/1992 | Coates et al. | 606/88 |
| 5,228,459 | 7/1993 | Caspari et al. | 128/898 |
| 5,234,433 | 8/1993 | Bert et al. | 606/88 |
| 5,250,050 | 10/1993 | Poggie et al. | 606/79 |
| 5,263,498 | 11/1993 | Caspari et al. | 128/898 |
| 5,304,181 | 4/1994 | Caspari et al. | 606/80 |
| 5,314,482 | 5/1994 | Goodfellow et al. | 623/20 |
| 5,474,559 | 12/1995 | Bertin et al. | 606/89 |
| 5,593,411 | 1/1997 | Stalcup et al. | 606/88 |
| 5,601,563 | 2/1997 | Burke et al. | 606/86 |

* cited by examiner

PROSTHETIC IMPLANT

RELATED APPLICATIONS

This is a continuation of application Ser. No. 08/892,286, filed Jul. 14, 1997 now U.S. Pat. No. 5,879,354, which was a divisional of U.S. patent application Ser. No. 08/649,465, filed May 17, 1996, now U.S. Pat. No. 5,755,803, which was a continuation-in-part application of U.S. patent application Ser. No. 08/603,582, filed Feb. 20, 1996, now U.S. Pat. No. 5,810,827 which was a continuation-in-part application of U.S. patent application Ser. No. 08/300,379, filed Sep. 2, 1994 by Goldstein et al., now U.S. Pat. No. 5,514,139, dated May 7, 1996.

U.S. patent application Ser. No. 08/603,582, filed Feb. 20, 1996, now U.S. Pat. No. 5,810,827, is also a continuation-in-part application of U.S. Ser. No. 08/479,363, filed Jun. 7, 1995, now U.S. Pat. No. 5,643,272 which is a continuation-in-part of U.S. patent application Ser. No. 08/342,143, filed Nov. 18, 1994 by Haines et al., now U.S. Pat. No. 5,597,379, which is a continuation-in-part application of U.S. patent application Ser. No. 08/300,379, filed Sep. 2, 1994, by Goldstein, et al., now U.S. Pat. No. 5,514,139, dated May 7, 1996. U.S. Ser. No. 08/479,363, now U.S. Pat. No. 5,643,272 is also a continuation-in-part of U.S. Ser. No. 08/300,379, Sep. 2, 1994, now U.S. Pat. No. 5,514,139. U.S. Ser. No. 08/603,582, now U.S. Pat. No. 5,810,872 is also a continuation-in-part application of U.S. Ser. No. 08/342,143 now U.S. Pat. No. 5,597,379 which is a continuation-in-part application of U.S. Ser. No. 08/300,379 now U.S. Pat. No. 5,514,139.

The entire disclosures of these related applications are expressly incorporated herein by reference.

BACKGROUND OF THE INVENTION

1. Field of the Invention

This invention generally relates to a prosthetic apparatus for augmenting a musculoskeletal structure for maintaining or improving said structure, and more particularly to a prosthetic implant for use in reconstructed or replacement knees or other joints.

2. Related Art

Different apparatus have been developed to enable a surgeon to replace damaged osseous and/or articular material of the muscoskeletal structure with prosthetic devices or structures in order to preserve or restore the structural or kinematic function of the body. Keeping in mind that the ultimate goal of any surgical procedure is to restore the body to normal function, it is critical that the quality and orientation of any bone cuts, as well as the quality of fixation, and the location and orientation of objects or devices attached to the bone, is sufficient to ensure proper healing of the body, as well as appropriate mechanical function of the musculoskeletal structure.

While the implant of the present invention has applications throughout the human body, the applications and embodiments shown and described herein are specifically configured for total knee replacement, a surgical procedure where planar or curvilinear surfaces are created in or on bone to allow for the proper attachment or implantation of prosthetic devices. It should be noted that the apparatus and methods set forth herein can modified and applied to any form of joint replacement wherein the function to be restored is dictated by both static and dynamic principles, as well as forms of muscoskeletal reconstruction which are dictated primarily by static principles of operation.

Currently, bony surfaces to be resected or cut are done so in a series of planar surfaces. In total knee replacement, a series of curvilinear surfaces or resections are created in the bone to allow the attachment of a number of prosthetic devices to the femur, tibia, and patella. In the case of the femur, the posterior and distal femoral condyles, the anterior femoral cortex, and other anatomic features are referenced to determine the location and orientation of the resections. The location and orientation of these resections are critical in that they dictate the quality of fixation of the prosthesis to the bone, as well as the final location and orientation of the prosthesis.

There are several major problems inherent in current implant designs caused directly by the need for interior and predominantly planar fixation surfaces (these surfaces are interior surfaces of the implant which mate with the resected bone) embodied in implant designs whose external geometry is predominantly curvilinear. These problems include:

a. the removal of excessive amounts of viable osseous tissues;

b. non-optimal or "unnatural" patellofemoral kinematics;

c. excessive implant rigidity resulting in stress shielding of living bone;

d. stress risers at the vertices of the planar fixation surfaces of the implant leading to potential failure sites under fatigue loading, and e. excessively massive implants resulting in additional material costs.

Past efforts have not been successful in properly addressing these concerns. Such previous efforts at implants are set forth in the following patents, none of which teach or suggest all of the benefits and advantages of the present invention. These previous patents include:

Goodfellow, et al., U.S. Pat. No. 5,314,482, discloses a femoral implant having a convexly shaped spherical articulation surface and a securement surface having major and minor areas at opposite end portions. The major area is essentially concavely spherically concentric with the articular surface to form a shell body part. The minor area is essentially planar and extends chordally of the articulation surface. The implant further includes a bone-penetrating pin extending radially from the major area in a direction parallel to the longitudinal direction of the minor area.

Walker, et al., U.S. Pat. No. 4,822,365, discloses a method of designing a prosthesis having convex male and concave female portions. The surface of the condylar male portion of the prosthesis is generated by analysis of either an average or specific condyle, or a distortion thereof to fit observed general dimensions of a specific patient. The female surface includes flexion and laxity surfaces. The flexion surfaces are generated by plotting the path of articulation of substantial points of contact between the male portion and a corresponding female portion. The laxity surfaces comprise raised guide-bearing surfaces for resisting dislocation of the condylar portion.

Hanslik, et al., U.S. Pat. No. 4,770,663, discloses a knee joint endoprosthesis comprising a femur with two skid surfaces and a space therebetween. The skid surfaces are interconnected at a front end. The skids having a curvature increasing from the front end to a rear end. The skids are also curved on planes perpendicular to the curvature. The joint endoprosthesis further comprises a tibia component having two surfaces on which the skids ride.

Zichner, et al., U.S. Pat. No. 4,662,889, discloses a knee joint prosthesis having a C-shaped a femur cap for attachment to a resected femur condyle. The cap includes an aperture therethrough for receiving a shaft. A cap is also placed over the tibia. A connecting member is implanted into the tibia and interconnected with the femur by the shaft.

Shoji, et al., U.S. Pat. No. 4,586,933, discloses a knee implant having a femoral component with a curved articulating surface, movable inserts positioned between the femoral component and a tibial tray, the inserts having concave articulating surfaces at the top and bottom thereof, and a tibial tray with convex tracks and posterior stops.

Johnson, et al., U.S. Pat. No. 4,568,348, discloses a knee prosthesis having a femoral component for attachment to the femur, a tibial component for attachment to the tibia and a meniscal component positioned therebetween. The tibial component has a concave bearing surface. The meniscal component has bearing surfaces complimentary to the tibial component and the femoral component. The femoral component has a two-part curved bearing surface including a first curved portion and a second curved posterior portion contiguous with and of relatively lesser curvature than the first curved portion.

Schurman, et al., U.S. Pat. No. 4,358,859, discloses a knee prosthesis comprising a femoral implant having a condyle section and a stem, and a tibial implant having a tibial plateau and a stop plate and a stem.

Forte, et al., U.S. Pat. No. 4,353,135, discloses a knee implant having a patellar flange comprising a curved base and a pair of condylar runners.

Russell, et al., U.S. Pat. No. 4,722,330, discloses a distal femoral surface guide for mounting on an intramedullary alignment guide for use in shaping the distal femoral surface. A conventional shaping means such as an oscillating saw or hand saw is introduced into slots in the surface guide to resect the femur. The device also includes stabilizing members that extend along the sides of the femur to stabilize the device. The attachment surface of the implant comprises a series of planar surfaces.

Lackey, U.S. Pat. No. 5,053,037, discloses a femoral drill guide with interchangeable femoral collets, a femoral reamer and a femoral anterior/posterior cutting block with an adoptable anterior femoral ledge. A plurality of diagonal slots are provided for making diagonal cuts in the distal end of the femur. The attachment surface of the implant comprises a series of planar surfaces.

Ferrante et al. U.S. Pat. No. 5,098,436, discloses a modular guide for shaping a femur comprising a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove and a portion of the selected area exposed through the opening. A second bracket defines a linear slotted bore extending generally parallel to the long axis of the femur for guiding a second shaping tool to form a relatively deep recess accommodating an intercondylar-stabilizing housing of a knee implant.

Poggie, et al., U.S. Pat. No. 5,250,050 discloses an apparatus for use in preparing the bone surfaces for a total knee prothesis, comprising cutting guides, templates, alignment guides, a distractor and clamping instruments. The instrument for alignment of the cutting surface for resecting the tibia includes an ankle clamp, an adjustable alignment rod, and a cutting platform. After the cutting platform is properly aligned on the tibia, it is pinned thereto and the tibia may be resected using an oscillating saw. Also disclosed is a patella resection guide comprising a scissor-type clamp having distal gripping arms, each of which define a cutting surface, and gripping teeth. The attachment surface of the implant comprises a series of planar surfaces.

Caspari, et al., U.S. Pat. Nos. 5,263,498, 5,228,459, and 5,304,181 disclose a method and apparatus for orthoscopically preparing bone surfaces for a knee replacement. A tibial jig is attached to the tibia at just above the ankle at a lower end and to just below the tibial tubercle at an upper end. One portal is formed in the knee for insertion of an orthoscope for viewing the knee, and another portal is formed for introducing resecting instruments. A cutting platform is aligned and secured in position and a cutting module is attached. Initially, a plunge cut across the tibial eminence is produced. This procedure is repeated until the surface of the tibial plateau is covered with trails having ridges therebetween. Thereafter, the device is passed back and forth over the tibial plateau to remove the ridges. The attachment surface of the implant comprises a series of planar surfaces.

Whiteside, U.S. Pat. No. 4,474,177 describes instruments for creating the distal femoral surfaces where a guide is used to index a flat surface used to guide the distal femoral resection. The attachment surface of the implant comprises a series of planar surfaces.

Kaufman, et al. U.S. Pat. No. 4,721,104 describes a method of preparing the intracondylar area of the distal femur. The attachment surface of the implant comprises a series of planar surfaces.

Collomb, European Application No. 538153-A1, discloses a modular device for positioning a knee prosthesis on a bone. The attachment surface of the implant comprises a series of planar surfaces.

Bert, et al., U.S. Pat. No. 5,234,433, discloses a method and apparatus for unicompartmental total knee arthroplasty. The attachment surface of the implant comprises a series of planar surfaces.

Pynaov, Russian Application No. 577,020, discloses an instrument for shaping the end joint of a bone to prevent arthrosis and ankylosis. The instrument is used to remove a central portion of the joint so that the joint ends are contacted in one plane without causing irritation in the paraarticular tissues. No implant structure is disclosed.

None of these previous efforts, however, disclose all of the benefits and advantages of the present invention, nor do these previous patents teach or suggest all the elements of the present invention.

OBJECTS AND SUMMARY OF THE INVENTION

It is a primary object of the present invention to provide an apparatus to properly replace damaged bony tissues.

It is also an object of this invention to provide an apparatus to properly replace damaged bony tissues in joint replacement surgery.

It is also an object of the present invention to provide an implant for the attachment to a distal femur in the context of knee replacement surgery.

It is an additional object of the present invention to provide a method and apparatus for making a curvilinear implant.

It is another abject of the present invention to provide an implant having a reduced thickness to reduce the amount of material required to make the implant.

It is even another object of the present invention to provide an implant having curvilinear fixation surfaces for increasing the strength of the implant.

It is another object of the present invention to provide an implant having a fixation surface that is anterior-posterior curvilinear and medio-lateral curvilinear.

It is another object of the present invention to provide an implant that has a fixation surface that is shaped to resemble a natural distal femur.

It is also an object of the present invention to provide an implant apparatus for allowing proper patellofemoral articulation.

It is a further object of the present invention to provide for minimal stress shielding of living bone through reduction of flexural rigidity.

It is an additional object of the present invention to provide an implant apparatus having internal fixation surfaces which allow for minimal bony material removal.

It is another object of the present invention to provide an implant apparatus with internal fixation surfaces that minimize stress risers.

It is another object of the present invention to provide an implant apparatus having internal fixation surfaces for precise fixation to curvilinear body resections.

It is another object of the present invention to provide an implant apparatus having internal fixation surfaces for precise apposition to curvilinear body resections.

It is another object of the present invention to provide an implant apparatus having internal fixation surfaces for curvilinear interior fixation geometries closely resembling the geometry of the external or articular geometry of the implant apparatus.

It is also an object of this invention to provide a method and apparatus for properly locating and orienting a prosthetic implant with respect to a bone.

It is another object of the present invention to provide an implant which is simple in design and precise and accurate in operation.

It is also an object of the present invention to provide an implant which minimizes the manual skill necessary to complete the procedure.

It is still yet another object of the present invention to provide an implant which minimizes the amount of bone removed.

It is even another object of the present invention to provide a method and apparatus for removing material from a bone such that both the cutting path and cutting profile are predominantly curvilinear.

These objects and others are met by the implant of the present invention which has an outer bearing surface and an inner attachment surface. The outer bearing surface functions as a joint contact surface for the reconstructed bone. The inner attachment surface contacts a bone and is attached thereto. The inner attachment surface of the implant is curvilinear from an anterior to a posterior area of the femur, as is conventionally known, and is also curvilinear from a medial to a lateral area of the femur to approximate the shape of natural femur. The resection of the femur for accommodating the implant can be properly performed by a milling device employing one or more curvilinear milling bits.

There are numerous advantages associated with the curvilinear implant of the present invention. First, it will allow for a very thin implant cross-section and therefore necessitate the removal of the least amount of viable osseous tissue. Accordingly, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs.

This curvilinear implant of the present invention could also result in a less expensive femoral implant because of the reduced amount of material needed for the implant, as well as an improved, more natural, and even stronger knee replacement. The cross-section of the implant could be varied to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces.

The resected surfaces of a femur or other bone to accept the implant of the present invention could be prepared by the apparatus and method for resection shown and described in the prior related applications set forth herein, the entire disclosures of which are expressly incorporated herein by reference.

BRIEF DESCRIPTION OF THE DRAWINGS

Other important objects and features of the invention will be apparent from the following Detailed Description ofthe Invention taken in connection with the accompanying drawings in which.

DETAILED DESCRIPTION OF THE INVENTION

The particular example of the present invention discussed herein relate to a prosthetic implant for attachment to a femur in the context of total knee arthroplasty, i.e. a femoral implant. However, it should be pointed out that the principles described herein may be applied to any other applications where foreign or indigenous material is affixed to any other anatomic feature.

Figure 1:
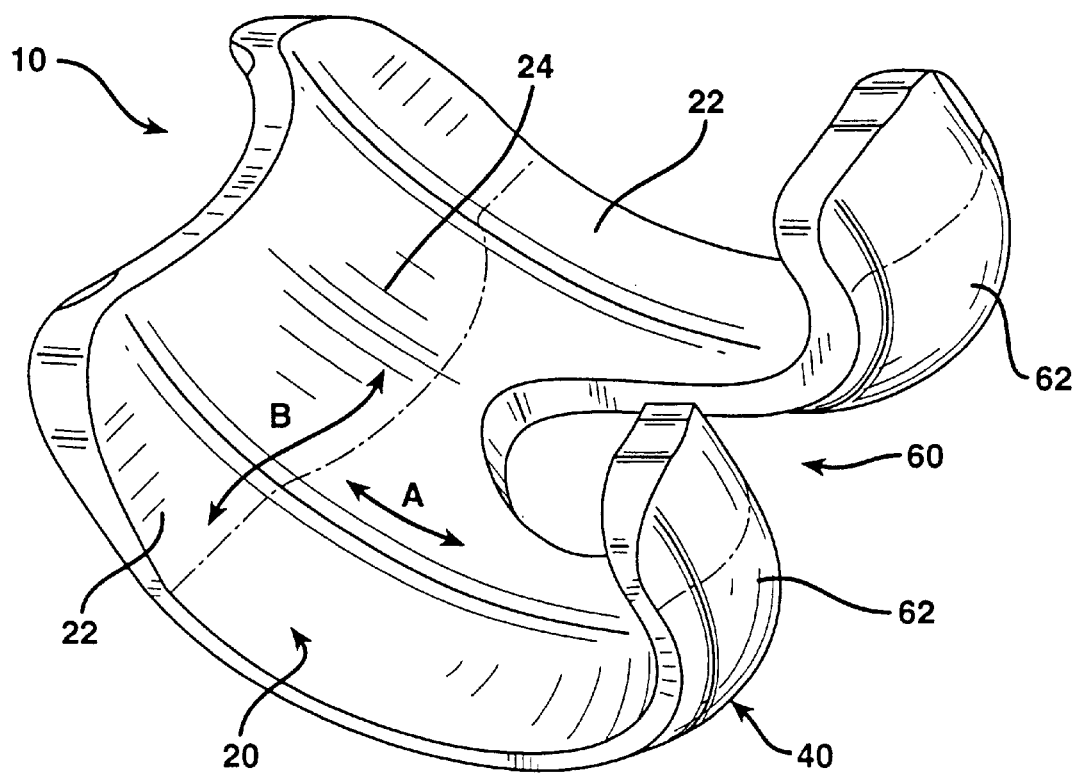
FIG. 1 is a perspective view of a femoral implant of the present invention having a curvilinear implant fixation surface.
Figure 2:
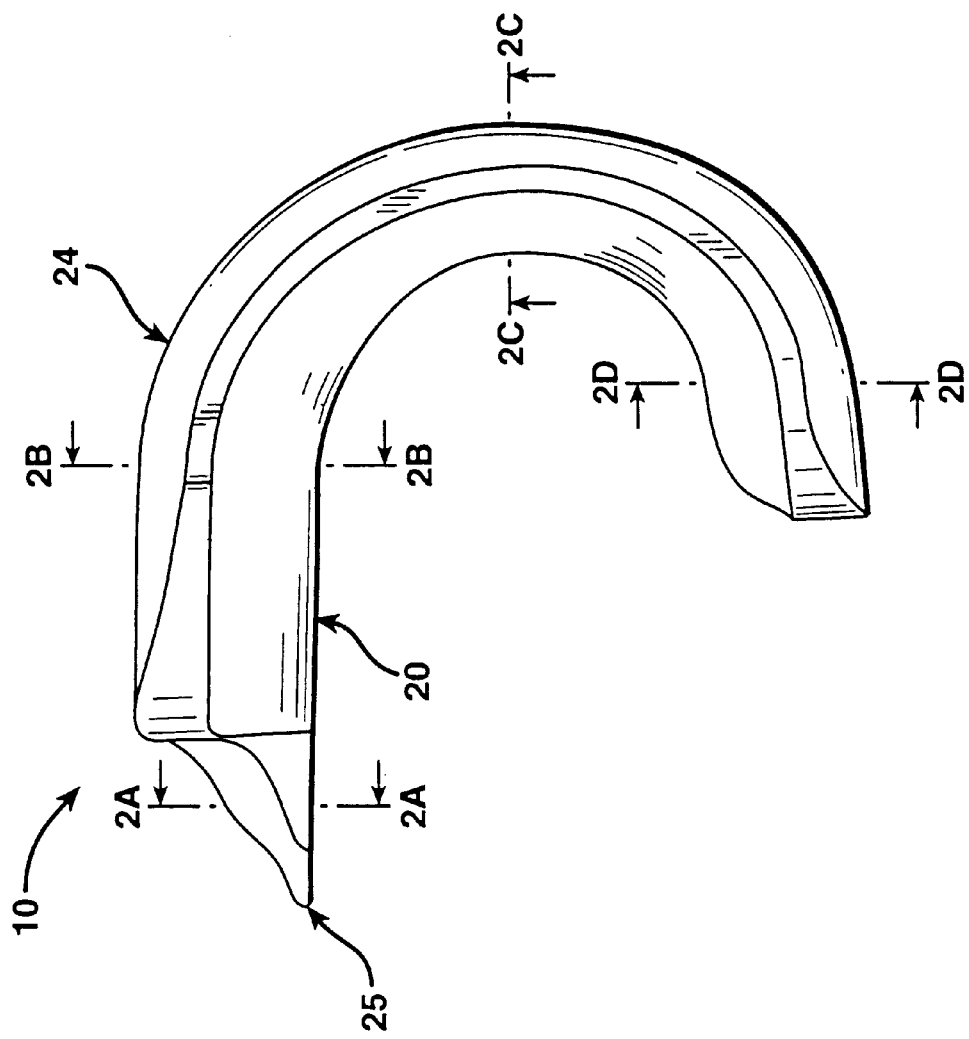
FIG. 2 is a side plan view of the femoral implant shown in FIG. 1, FIGS. 2A, 2B, 2C and 2D being sectional views taken along lines A—A, B—B, C—C and D—D of FIG. 2, respectively.
Figure 2A:
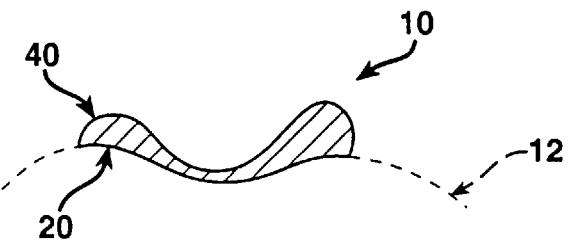
Figure 2B:
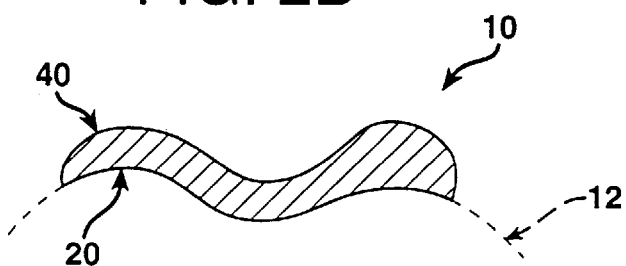
Figure 2C:
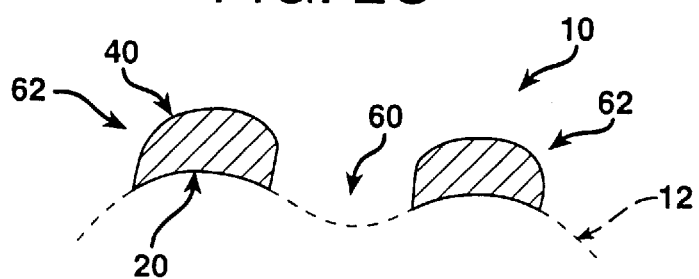
Figure 2D:
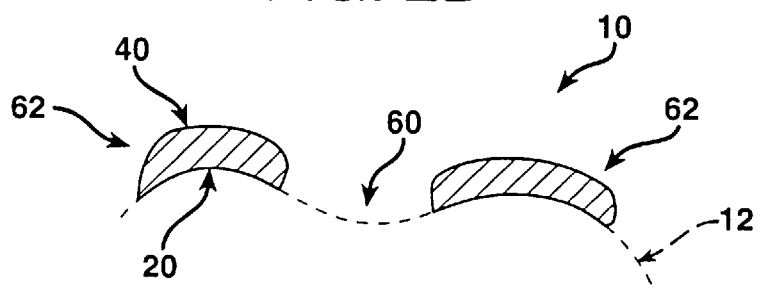

As shown generally in FIGS. 1 and 2, the implant apparatus of the present invention, generally indicated at 10, comprises curvilinear interior fixation surface 20 as well as curvilinear exterior bearing surface 40. Importantly, the implant of the present invention includes curvilinear surfaces extending from an anterior to a posterior area of the femur and/or implant, as is conventionally known, as well as curvilinear surfaces extending from a medial to a lateral area of the femur and/or implant to approximate the shape of natural femur. In other words, the fixation path (i.e. corresponding to the cutting path along which the milling bit rides to resect the femur; indicated by arrow A in FIG. 1) as well as the fixation profile (as one proceeds along the cutting profile orthogonally to the cutting path; indicated by arrow B in FIG. 1) are both predominantly curvilinear. As such, the cutting profile (arrow B) of the interior fixation surface 20 could include a curved or flat 22 and another curved or flat area 24 therebetween. Preferably, the outer areas 22 are flat or relatively flat and the inner area 24 is curved to approximate the shape of a natural distal femur 12. It should be pointed out the outer areas 22 could be curved, and the inner area 24 could also be curved, but embodying differing radii of curvature. Additionally, it should be pointed out the geometry of the internal fixation surface 20 of the implant 10 could be varied as desired. As such, any combination of flat surfaces and curvilinear surfaces could be used. As shown in FIG. 2, and in more detail in FIGS. 2A, 2B, 2C and 2D, the cross-sectional thickness and medio-lateral width of the implant of the present invention could vary along the implant 10. This variance results from merging a cutting tool to cut a bone, i.e., the implant 10 closely resembles in size and shape the material removed from the bone. Accordingly, the cut starts as a point 25 and grows in depth and width.

Figure 3:
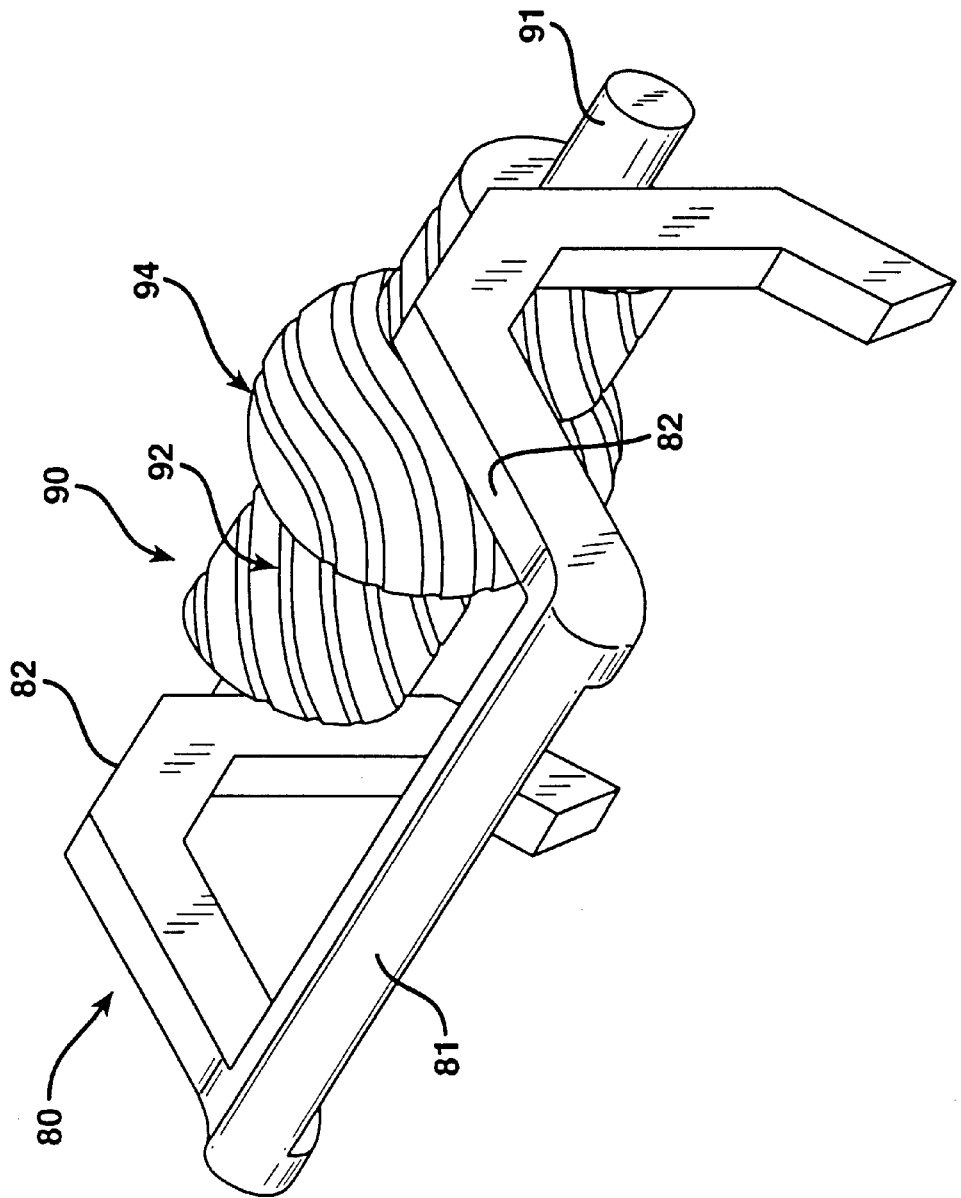
FIG. 3 is a perspective view of a curvilinear milling bit and resection guide for creating a curvilinear resection in a bone for accepting the curvilinear implant shown in FIG. 1.
Figure 4:
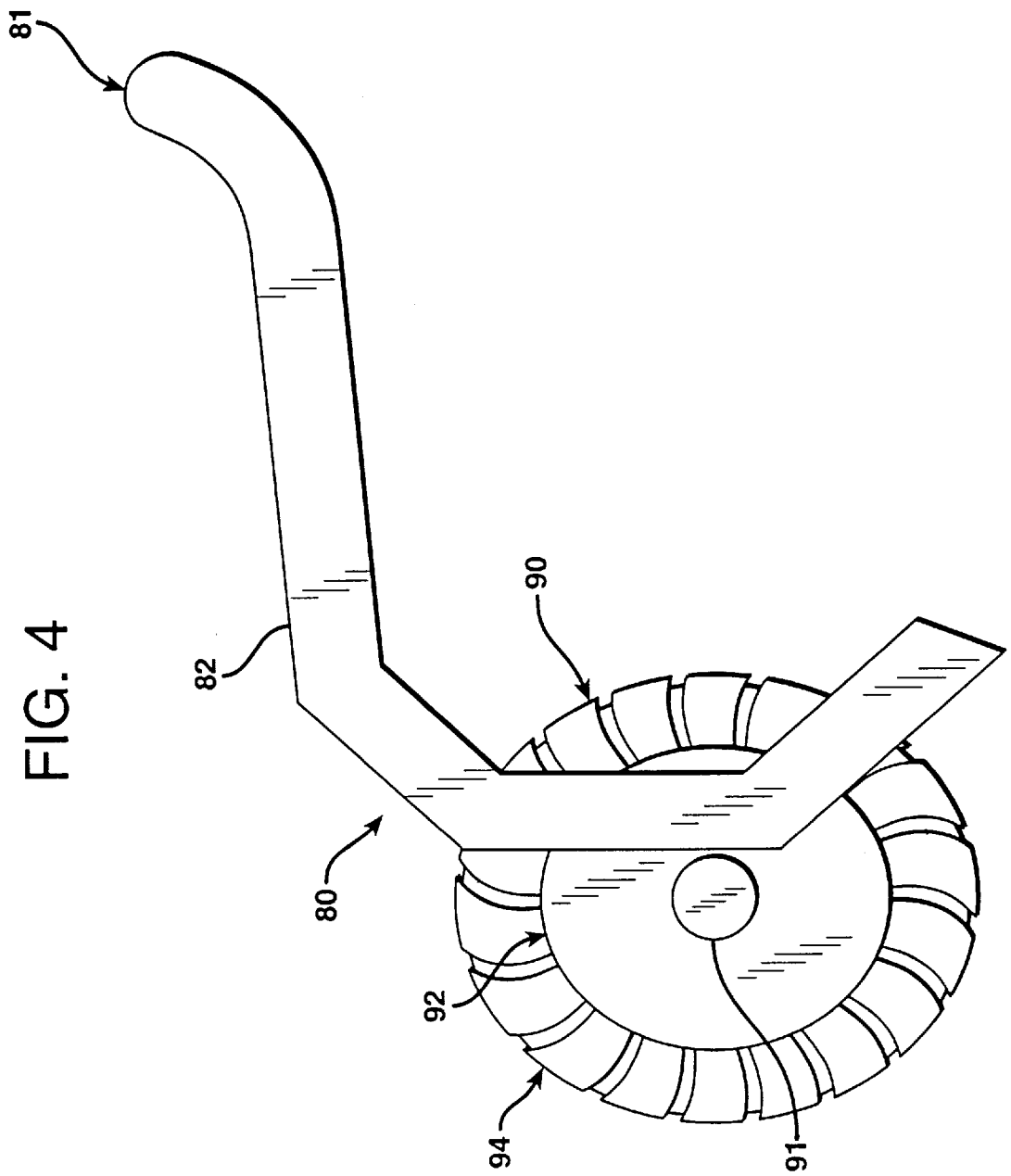
FIG. 4 is a side plan view of the curvilinear milling bit and resection guide shown in FIG. 3.

The curvilinear bone surfaces necessary for proper fixation of such an implant 10 may be generated through the use of the curvilinear milling bit or form cutter and the curvilinear cutting path means discussed in the previous related applications set forth herein, the entire disclosures of which are expressly incorporated herein by reference. Basically, the milling bit has a profile resulting in form cutter configuration which is concentric about its longitudinal axis to effect a curvilinear cutting profile for receiving the implant of the present invention. One embodiment of such a form cutter is shown in FIGS. 3 and 4. While it is possible to use multiple form cutters with differing geometries and therefore an implant 10 with an internal geometry that varies along the cutting path from the anterior to the posterior of a femur, for the sake of intraoperative time savings, a single anatomically optimal form cutter is preferable.

The form cutter shown in FIGS. 3 and 4 comprises a cutting guide 80 having a cutting paths 82 interconnected by member 81. A milling bit 90 having cylindrical milling areas 92 at the ends, and a curved milling area 94 at the center could be used. Of course, the milling areas carry cutting teeth. Spindles 91 interconnected at each end of the milling bit 90 could engage and ride the cutting path 82 of the cutting guide 80. The milling bit 90 is then guided along the cutting path 82 by means of a handle. Importantly, the shape of the milling bit 90 could be varied as desired to create a resection having a desired cutting path as well as a desired cutting profile.

The medio-lateral cross-sectional internal geometry of such an implant 10, and therefore the necessary resected bony surfaces of the femur, are consistent about the cutting path in a single form cutter system. It should be noted that the implant 10 may possess a notch 60 between members 62 (posterior femoral implant condyles) in the areas approximately between the distal and posterior femoral condylar areas to accommodate the posterior cruciate ligament, as well as for other reasons. Because of the notch 60 between the posterior femoral condyles, the form cutter may not cut any material in the notch 60.

Figure 5:
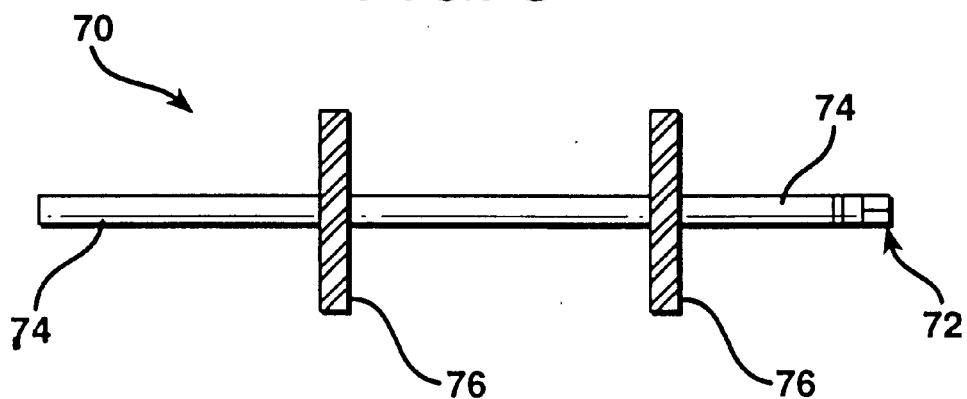
FIG. 5 is a perspective view of another embodiment of a milling bit for creating a resection in a bone for accepting the curvilinear implant of the present invention.

Additionally, it may be advantageous to utilize a secondary form cutter as shown in FIG. 5 for use in creating a slot or slots in or near the distal area of the femur before or after it has been resected. Such a secondary cutter 70 would include engagement means 72 for engagement with driving means, and a shaft 74 carrying one or more cutters 76 for cutting slots into the femur through one or more of the resected surfaces thereof.

Figure 6:
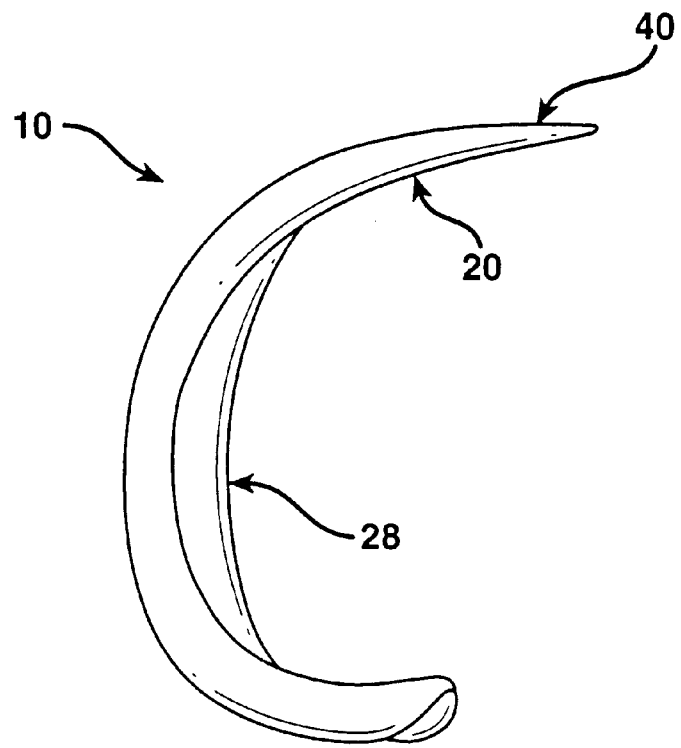
FIG. 6 is a side plan view of another embodiment of the femoral implant shown in FIG. 1.

Through the inclusion of an additional or adjunct cutting path in the pattern means, it would be advantageous to utilize the form cutter to create the aforementioned slots in the distal femur to accommodate the fixation fins which may be molded as an integral part of the interior surface of the implant 10. An implant with fixation fins is shown in FIG. 6. The fins 28 would provide medio-lateral fixation stability in addition to that provided by the trochlear groove geometry of the implant 10. Further, the fins also provide for additional surface area for bony contact and ingrowth to increase implant fixation both in cemented and cementless total knee arthroplasty.

Figure 7:
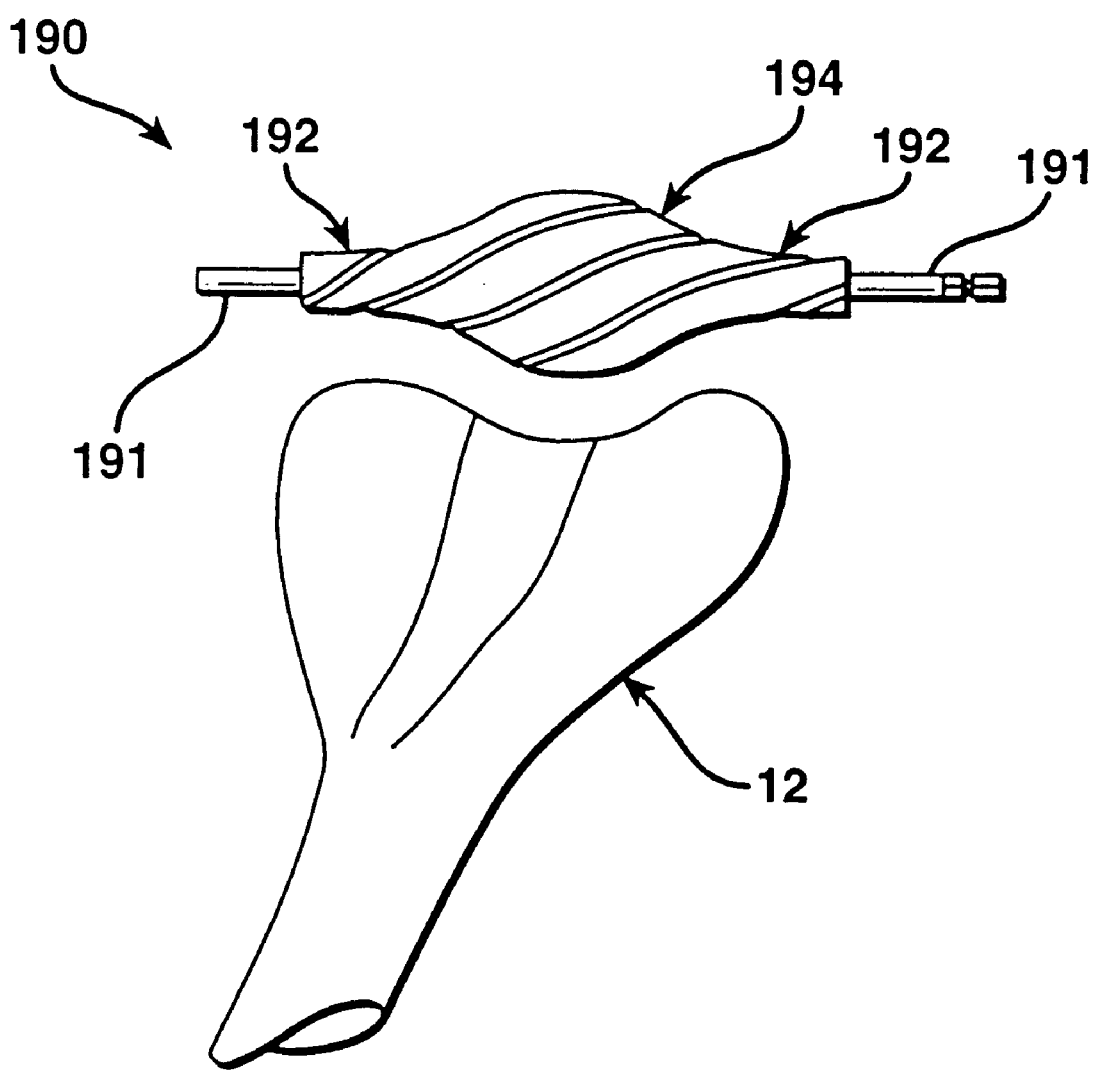
FIG. 7 is a front plan view of another curvilinear milling bit for creating a curvilinear resection in a bone for accepting the curvilinear implant shown in FIG. 1.

FIGS. 7 shows another embodiment of a milling bit, generally indicated at 190 for creating a curvilinear cutting path and curvilinear cutting profile in femur 12. In this embodiment, the transition from a first cutting area 192 to a second cutting area 194 is continuous and smooth. This milling bit 190 also includes spindles 191 at the ends thereof for engagement with pattern means to guide the milling bit along a cutting path.

There are numerous advantages to the femoral component herein described. Foremost, it will allow for the thinnest implant cross-section possible (perhaps 3 mm to 6 mm in nominal thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint.

In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. The implant could have a relatively consistent cross-sectional thickness throughout the implant, or it could be varied as desired.

The curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e. when a cast is placed on a person's arm the muscles in that arm gradually weaken for lack of use.

Further, the curvilinear implant of the present invention could allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant would not only allow for the superior surface properties of ceramic, but also avoid the excessively thick cross-sections currently required for the use of the material.

The curvilinear implant of the present invention could result in a less expensive femoral implant because of the reduced amount of material needed for the implant, as well as an improved, more natural, and even stronger knee replacement. It may desirable to vary the cross-section of the implant to assist in seating the implant, to increase the joint kinematics and to increase the strength and fit of the implant. The implant of the present invention could be fabricated of metal, plastic, or ceramic or any other material or combination thereof. Further, the thickness of the implants and the material required to fabricate the implant could be reduced as the implants are adapted to increasingly curvilinear surfaces. Also, it should be pointed out that such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Importantly, by using a milling bit having a curved profile, one can cut a femur to resemble the natural shape of the femur, i.e. the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof as shown in FIGS. 3 and 4, or alternatively, could have one or more bulges discretely formed along the length thereof Modifications of the foregoing may be made without departing from the spirit and scope of the invention. What is desired to be protected by Letters Patents is set forth in the appended claims.

What is claimed is:

1. A prosthetic implant for attachment to a resected femur for total knee arthroplasty comprising:
    an outer bearing surface having a three dimensionally curved geometry and including a patellar groove;
    an inner contact surface having a three dimensionally curved geometry, said geometry curved along a medio-lateral direction and an anterior-posterior direction; said inner contact surface including an inner patellar groove area, said inner patellar groove area being of a three dimensionally curved geometry, said geometry curved along a medio-lateral direction and an anterior posterior direction; and
    said inner contact surface geometrically corresponding to a geometry of a resected femur having a three dimensionally curved geometry, for full contact and attachment of said inner contact surface with a resected femur.

2. The implant of claim 1 wherein the inner contact surface geometrically approximates the outer bearing surface.

3. The implant of claims 1 wherein the inner contact surface geometrically matches the outer bearing surface.

4. The implant of claim 1 wherein the inner contact surface approximates the geometry of a non-resected bone to be reconstructed.

5. The implant of claim 4 wherein the inner contact surface fully contacts the curved surfaces of a bone are formed by at least one milling bit having a curvilinear profile.

6. The implant of claim 1 wherein the anterior-posterior curvature of the inner contact surface varies along the implant to approximate the geometry of a bone.

7. The implant of claim 1 wherein the thickness of the implant between the outer bearing surface and the inner contact surface is uniform for the implant.

8. The implant of claim 1 wherein fins are interconnected with the inner contact surface of the implant.

9. A prosthetic implant for attachment to a resected bone comprising:
    an outer bearing surface;
    an inner contact surface including inner medial and lateral condylar areas;
    each of said inner medial and lateral condylar areas being of a three dimensionally curved concave geometry, said concave geometry curved along a medio-lateral direction and an anterior-posterior direction;
    each of said inner medial and lateral condyle areas interconnected by an inner patellar groove area, said inner patellar groove area being of a three dimensionally curved convex geometry, said convex geometry curved along a medio-lateral direction and an anterior posterior direction; and
    said inner contact surface geometrically corresponding to a geometry of a resected femur having a three dimensionally curved convex medial and lateral condylar geometry, and a three dimensionally curved concave patellar groove geometry, for full contact and attachment of said inner contact surface with a resected femur.

10. The implant of claim 9 wherein the inner contact surface geometrically approximates the outer bearing surface.

11. The implant of claims 9 wherein the inner contact surface geometrically matches the outer bearing surface.

12. The implant of claim 9 wherein the inner contact surface approximates the geometry of a non-resected bone to be reconstructed.

13. The implant of claim 9 wherein the inner contact surface fully contacts the curved surfaces of a bone are formed by at least one milling bit having a curvilinear profile.

14. The implant of claim 9 wherein the anterior-posterior curvature of the inner contact surface varies along the implant to approximate the geometry of a bone.

15. The implant of claim 9 wherein the thickness of the implant between the outer bearing surface and the inner contact surface is uniform for the implant.

16. The implant of claim 9 wherein fins are interconnected with the inner contact surface of the implant.

* * * * *